(12) United States Patent
Talbot et al.

(10) Patent No.: US 8,998,178 B2
(45) Date of Patent: Apr. 7, 2015

(54) SCENT PAD AND MECHANISM FOR HOUSING THE SAME

(75) Inventors: Janet Talbot, Uxbridge, MA (US); Lara Peterson, Mendon, MA (US)

(73) Assignee: Helen of Troy Limited, St. Michael (BB)

( * ) Notice: Subject to any disclaimer, the term of this patent is extended or adjusted under 35 U.S.C. 154(b) by 259 days.

(21) Appl. No.: 13/572,418

(22) Filed: Aug. 10, 2012

(65) Prior Publication Data

US 2014/0041524 A1  Feb. 13, 2014

(51) Int. Cl.
*B01F 3/04* (2006.01)
*A61L 9/03* (2006.01)
*A61L 9/12* (2006.01)
*F24F 3/12* (2006.01)
*F24F 6/02* (2006.01)
*F24F 3/16* (2006.01)

(52) U.S. Cl.
CPC ... *A61L 9/03* (2013.01); *A61L 9/12* (2013.01); *F24F 3/12* (2013.01); *F24F 6/025* (2013.01); *A61L 2209/133* (2013.01); *F24F 2003/1689* (2013.01); *Y10S 261/88* (2013.01)

(58) Field of Classification Search
USPC ............ 261/95, 101, 142, DIG. 88, DIG. 89; 96/222; 239/136, 55
See application file for complete search history.

(56) References Cited

U.S. PATENT DOCUMENTS 6,102,300 A * 8/2000 Bruckner et al. ............... 239/55
8,770,557 B2 * 7/2014 Kanel .......................... 261/142

FOREIGN PATENT DOCUMENTS

| EP | 2452557 | 5/2012 |
| EP | 2664348 | 11/2013 |
| WO | 2006/135647 | 12/2006 |
| WO | 2011/042232 | 4/2011 |
| WO | 2012/078973 | 6/2012 |
| WO | 2013/012442 | 1/2013 |

OTHER PUBLICATIONS

Partial European Search Report from European Patent Application No. 13180116 mailed on Mar. 5, 2014.

* cited by examiner

*Primary Examiner* — Robert A Hopkins
(74) *Attorney, Agent, or Firm* — Stroock & Stroock & Lavan LLP

(57) ABSTRACT

An improved scent pad and mechanism for housing the same. The mechanism is preferably a part of a humidifier or similar device and positioned adjacent to a heated surface. The mechanism preferably includes a cover, a keyed portion and a rib portion which allows the scent pad to fit properly and prevents other shaped pads from being inserted into or otherwise used in the housing mechanism, insuring optimal performance. In one embodiment the scent pad includes an upper straight edge, side edges, two lower beveled edges and a lower straight edge situated between the beveled edges. The upper straight edge and lower straight edge are preferably substantially parallel to each other. The side edges are preferably substantially parallel to each other and the beveled edges are preferably arranged at an angle that intersects both the lower straight edge and a side edge.

20 Claims, 3 Drawing Sheets

SCENT PAD AND MECHANISM FOR HOUSING THE SAME

BACKGROUND OF THE INVENTION

1. Field of the Invention

The present invention generally relates to a scent pad and mechanism for housing the same.

2. Description of Related Art

The ability to easily and efficiently control indoor environments is highly desirable. For this reason, a number of devices have been developed to control the temperature, humidity, odor and air quality of enclosed environments such as the rooms of a house. These devices include humidifiers, air purifiers, heaters, fans, scent masks, air fresheners and the like.

For example, in temperate climates controlling humidity can be very important. During the winter and the months surrounding the winter, a lack of humidity in the air can cause significant discomfort to people. Humidifiers are a typical device used to control humidity. During these same months, many people develop colds and have sinus and chest congestion. One method for treating congestion and colds is by dispersing a soothing menthol scent into the air.

Humidifiers including means for generating a scent have been developed but have various drawbacks. These humidifiers typically include an air freshener portion to disperse an aesthetic scent into the environment. Known humidifiers having an air freshening capability include humidifiers with scented objects disposed in an air path generated by a fan of the humidifier. The scented object continuously diffuses a scent into the air and the fan blows the scent into the surrounding environment. These scented objects known as "scent pads" typically are of a parallelogram shape such as a square or rectangle and are inserted into a slot or holder within the humidifier that is located adjacent to the fan and against a heated surface which releases the scented materials into the air.

In prior art devices, these slots or holders within the humidifier fit any scent pads or other materials that a user would insert. Thus, the manufacturer of a humidifier could not control what pads are used with which particular humidifiers. Use of improper scent pads or pads that were not optimized for the particular device would result in inferior performance and could result in damage to the humidifier.

There is a need for a mechanism for ensuring that a particular scent pad is used with a humidifier component for housing such a scent pad. This component should be specially designed to house a specially shaped pad. Such a mechanism would help ensure that the pad can be optimized for the particular humidifier based on shape, material thickness and the like.

It should be noted that although the description herein describes the mechanism for housing the scent pad of the present invention as being a part of a humidifier, it can be appreciated by one of ordinary skill in the art that certain aspects of the present invention can be used in conjunction with other devices such as a heater, air purifier or a fan for example.

SUMMARY OF THE INVENTION

In view of the above discussion and the shortcomings in the prior art, the invention seeks to overcome such shortcomings of the prior art by providing an improved scent pad and a mechanism for housing the same.

According to one embodiment of the present invention the scent pad includes an upper straight edge, side edges, two lower beveled edges and a lower straight edge situated between the beveled edges. The upper straight edge and lower straight edge are preferably substantially parallel to each other. The side edges are preferably substantially parallel to each other and the beveled edges are preferably arranged at an angle that intersects both the lower straight edge and a side edge.

According to another embodiment of the present invention the scent pad includes an upper straight edge, side edges, two lower side edges, extensions that connect the side edges to the lower side edges and a lower straight edge situated between the lower side edges. The upper straight edge, extensions and lower straight edge are preferably substantially parallel to each other. The side edges are preferably substantially parallel to each other and to the lower side edges.

In another embodiment a mechanism for housing a scent pad is disclosed. The mechanism is preferably a part of a humidifier or similar device and is positioned adjacent a heated surface of the humidifier so that the scent or other materials in the pad can be released into the air. The mechanism preferably includes a top cover, a keyed portion and a rib portion which allows the scent pad to fit properly and prevents other shaped pads from being inserted into or otherwise used in the housing mechanism, insuring optimal performance.

BRIEF DESCRIPTION OF THE DRAWINGS

Certain embodiments of the present invention, will be better understood when read in conjunction with the appended drawings wherein like reference numerals refer to like components. For the purposes of illustrating the present application, there is shown in the drawings preferred embodiments. It should be understood and appreciated, however, that the application is not limited to the precise arrangements, structures, features, embodiments, aspects, and devices shown, and the arrangements, structures, features, embodiments, aspects and devices shown and may be used singularly or in combination with other arrangements, structures, features, embodiments, aspects and devices.

The drawings are not necessarily drawn to scale and are not in any way intended to limit the scope of this invention, but merely to clarify a single illustrated embodiment of the invention. In the drawings.

DETAILED DESCRIPTION OF THE PREFERRED EMBODIMENTS

Certain exemplary embodiments of the invention will now be discussed with reference to the aforementioned figures. In general, such embodiments relate to a scent pad and a mechanism for housing the same within a humidifier, although as one of ordinary skill in the art can appreciate, certain embodiments of the present invention can be utilized in connection with various other devices such as a heater, fan, air purifier or the like.

Figure 1:
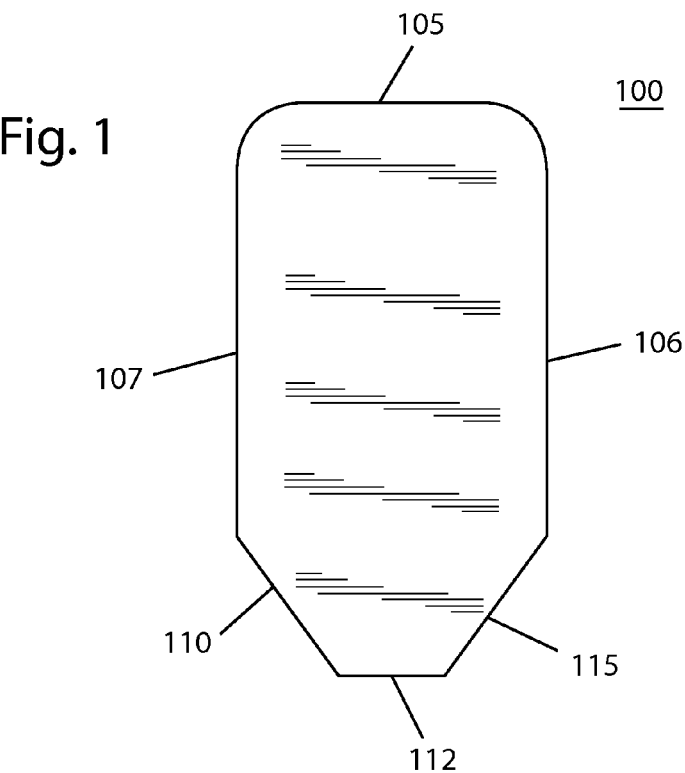
FIG. 1 is a front view of a scent pad according to one embodiment of the present invention.

As can be seen in FIG. 1, scent pad 100 includes an upper straight edge 105 and side edges 106 and 107. Scent pad 100 also includes lower beveled edges 110 and 115 and lower straight edge 112. Upper edge 105 and lower straight edge 112 are preferably substantially parallel to each other. Side edges 106 and 107 are preferably substantially parallel to each other and substantially perpendicular to upper edge 105 and lower straight edge 112. As can be further seen in FIG. 1, beveled edges 110 and 115 are preferably arranged at an angle that intersects both lower edge 112 and side edges 106 and 107.

Figure 1A:
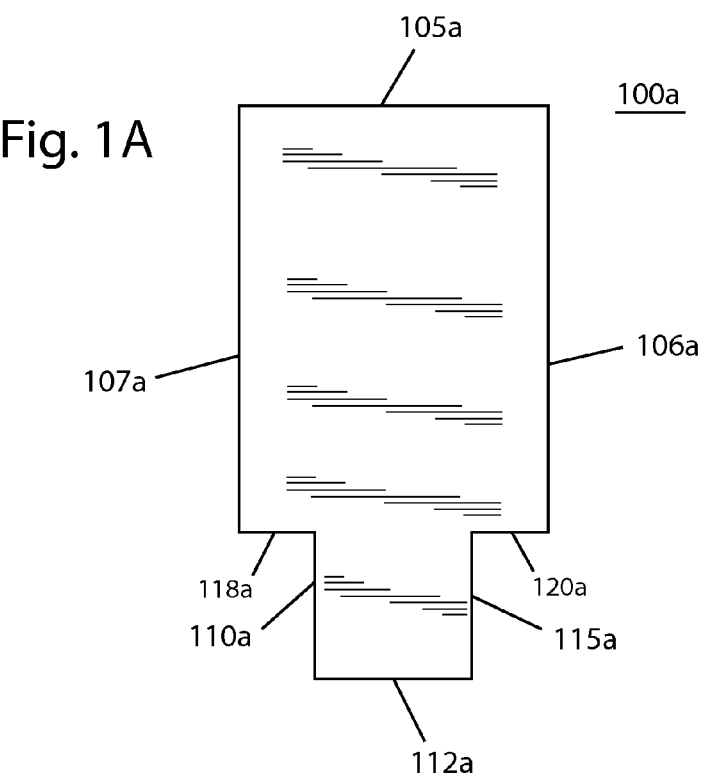
FIG. 1A is a front view of a scent pad according to an alternative embodiment of the present invention.

In an alternative embodiment as can be seen in FIG. 1A, scent pad 100a includes an upper straight edge 105a and side edges 106a and 107a. Scent pad 100a also includes lower straight edges 110a and 115a and lower straight edge 112a. Upper edge 105a and lower straight edge 112a are preferably substantially parallel to each other. Side edges 106a and 107a are preferably substantially parallel to side edges 106a and 107a and substantially perpendicular to upper edge 105a and lower straight edge 112a. As can be further seen in FIG. 1A, side edge 110a is preferably attached to side edge 107a via extension 118a and side edge 115a is preferably attached to side edge 106a via extension 120a. Extension 118a and 120a are substantially perpendicular to side edges 106a, 107a, 110a and 115a.

The scent pad is preferably made from a porous material that may include wood, cotton or synthetic fibers and can include oil or alcohol based scent ingredients. The scent pads may have a purely aesthetic scent, such as a floral or citrus scent, or a soothing scent such as lavender, rosemary, or menthol. In operation the scent pad can be heated to or placed in the path of a fan in a humidifier or similar device so as to release a scent into the atmosphere. Typically the scent pads are designed to release a scent, and release of the scent is enhanced by heating the scent pads. This heating typically involves placing the scent pad in a holder that is in the vicinity of a heated surface on the humidifier.

Figure 2:
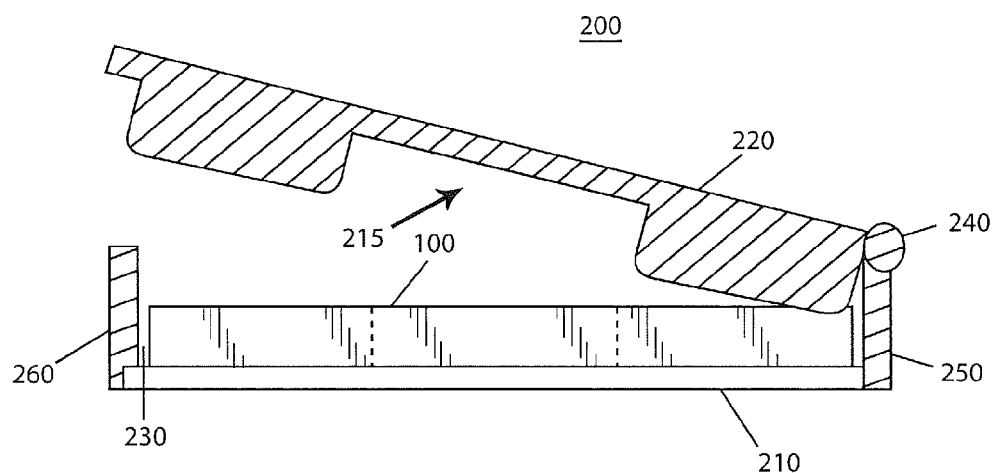
FIG. 2 is a side view of the mechanism for housing the scent pad in an open position according to one embodiment of the present invention.

As can be seen in FIG. 2 the humidifier typically has a heated surface 210 onto or next to which scented pad 100 can be placed. Although the below embodiment discusses the placement of a pad in the shape of scented pad 100, it will be appreciated by one of ordinary skill in the art that in alternative embodiments, the mechanism for housing the scented pad can be designed and/or altered to receive different shaped pads such as pad 100a. According to one embodiment, the mechanism 200 for housing the pad 100 includes top cover 220 that has a keyed portion 215 which mates with and covers pad 100 once the pad is in place and the cover is in a closed position. Keyed portion 215 prevents other pads of differing shapes from being placed into the slot 230. In other words, if a scent pad that has a different shape than pad 100 is placed into slot 230, cover 220 will not be able to close. Cover 220 is preferably attached via a hinge 240 to a stationary vertical bar 250 allowing cover 220 to move from an open position to a closed position. Mechanism 200 further includes a second vertical bar 260 that comes in contact with cover 220 when it is in a closed position to enclose pad 100. Although shown as being attached by a hinge, cover 220 can be attached or removably detached from vertical bar 250 or other portion of the humidifier as can be appreciated by one of ordinary skill in the art. Moreover although shown as part of the cover 220, the ribbed portion and or keyed portion may be separate from cover 220. Alternatively, the cover can be eliminated when the pad is held in place and fitted by a standalone ribbed and/or key portion.

Figure 3:
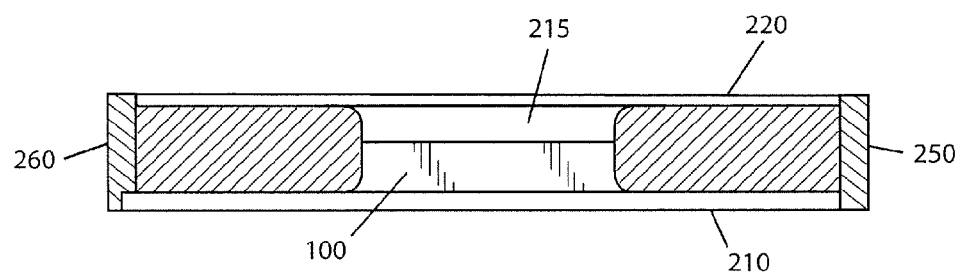
FIG. 3 is an end view of the mechanism for housing the scent pad in a closed position according to one embodiment of the present invention.

FIG. 3 shows an end view of mechanism 200 in its closed position. As can be seen in FIG. 3, when top cover 220 is in its closed position, keyed portion 215 mates with pad 100 so that only a scent pad that has a specific shape (e.g., the beveled surfaces of pad 100) can be retained on heated surface 210. In contrast, a scent pad that has a parallelogram or circular shape will not fit within mechanism 200 in the same way that scent pad 100 does. In an alternative embodiment, cover 200 can be made of two or more separate pieces each of which can be attached to vertical bar 250 and 260 respectively. Once each portion of the cover is moved into a closed position, together they secure pad 100 to heated surface 210 and prevent pads of other shapes from being used in this mechanism.

Figure 4:
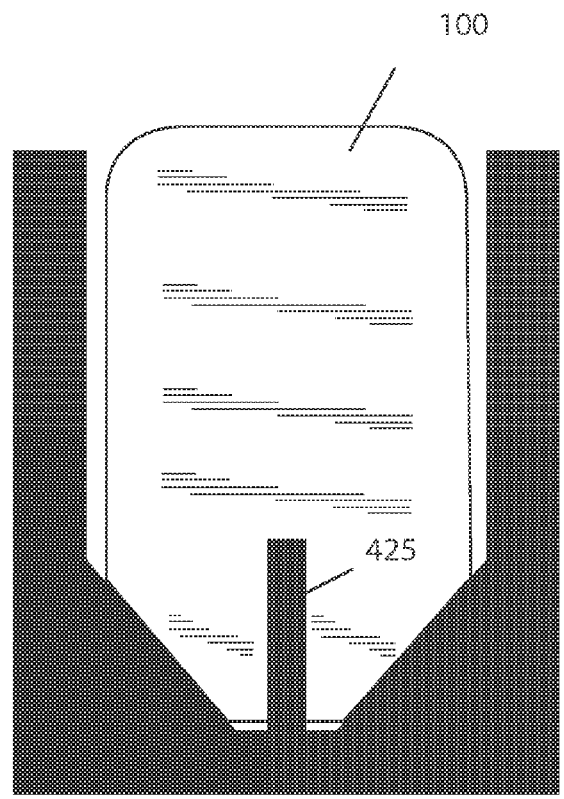
FIG. 4 is a front cutaway section view of the mechanism for housing the scent pad according to one embodiment of the present invention.
Figure 5:
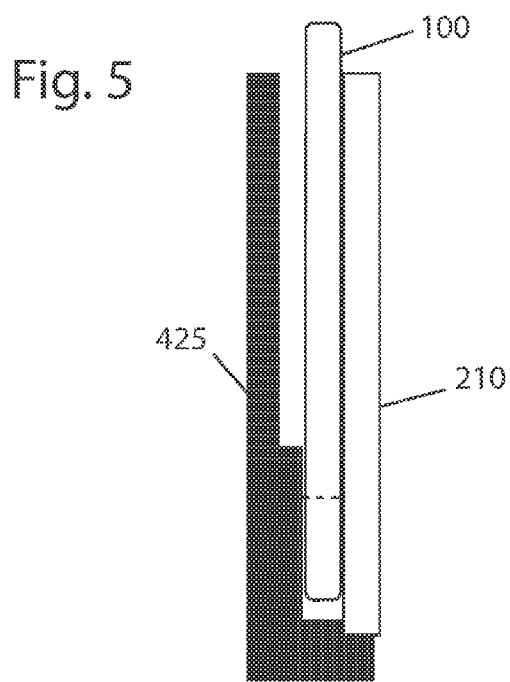
FIG. 5 is a side cutaway section view of the mechanism for housing the scent pad according to one embodiment of the present invention.

FIGS. 4 and 5 shows a front cutaway view and side cutaway view of mechanism 200 respectively which has a keyed slot into which pad 100 may be inserted. As can be seen in FIGS. 4 and 5, rib portion 425 holds pad 100 against heated surface 210 so that it cannot move. Rib portion 425 also conforms to the shape of scent pad 100. If a scent pad that has a different shape than pad 100 (e.g., does not have the beveled surfaces of pad 100), it will not be able to be placed past the rib portion 425 and hence will not be held against heated surface 210 as required to allow the scented pad to release its scent in a most efficient manner as is known in the art. Rather, rib portion 425 will obstruct insertion of such misshaped scent pad and will not allow it to be completely inserted.

One having ordinary skill in the art will recognize that the various mechanisms described for the preferred embodiments of the scent pad and humidifier may be adapted and interchanged between the preferred embodiments, without significantly impacting the structure and operation of the invention. Those skilled in the art will recognize that the present invention has many applications, may be implemented in many manners and, as such is not to be limited by the foregoing embodiments and examples.

Any number of the features of the different embodiments described herein may be combined into one single embodiment, the locations of particular elements can be altered and alternate embodiments having fewer than or more than all of the features herein described are possible. Functionality may also be, in whole or in part, distributed among multiple components, in manners now known or to become known.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention. While there had been shown and described fundamental features of the invention as applied to being exemplary embodiments thereof, it will be understood that omissions and substitutions and changes in the form and details of the disclosed invention may be made by those skilled in the art without departing from the spirit of the invention. Moreover, the scope of the present invention covers conventionally known, future developed variations and modifications to the components described herein as would be understood by those skilled in the art.

The invention claimed is:
1. An air treatment device comprising:
a housing;

a receptacle within the housing, the receptacle having a keyed portion and a rib portion being provided as part of a cover;

wherein the receptacle is configured and dimensioned to receive a first shaped pad so that when the cover of the receptacle is in a closed position it covers at least a portion of the first shaped pad and the first shaped pad is brought into contact with the rib portion.

2. The air treatment device of claim 1 wherein the cover is connected to the receptacle.

3. The air treatment device of claim 2 wherein the cover is pivotally connected to the receptacle.

4. The air treatment device of claim 1 wherein when the cover is in a closed position, it covers the entire first shaped pad.

5. The air treatment device of claim 1 wherein the pad is a scented pad.

6. The air treatment device of claim 1 further comprising a heated surface that is in contact with the receptacle.

7. The air treatment device of claim 1 wherein the pad comprises:
an upper straight perimeter;
a first side perimeter;
a second side perimeter substantially parallel to the first side perimeter;
a first lower beveled perimeter;
a second lower beveled perimeter; and
a lower straight perimeter substantially parallel to the upper straight perimeter and substantially perpendicular to the first side perimeter wherein the lower straight perimeter is situated between the first lower beveled perimeter and the second lower beveled perimeter.

8. The air treatment device of claim 1 wherein the air treatment device is a humidifier.

9. The air treatment device of claim 1 wherein the air treatment device is a heater.

10. The air treatment device of claim 1 wherein the air treatment device is a fan.

11. The air treatment device of claim 1 wherein the air treatment device is an air purifier.

12. A receptacle within an air treatment device comprising:
a bottom surface;
a pivotable cover pivotally moveable with respect to the bottom surface;
a keyed portion; and
a rib portion;
wherein the keyed portion and the rib portion are configured and dimensioned to enclose a first shaped pad when the cover and bottom surface are brought in contact with each other in a closed position.

13. The receptacle of claim 12 wherein when the cover is in a closed position, it covers the entire first shaped pad.

14. The receptacle of claim 12 wherein the keyed portion and the rib portion are provided as part of the cover.

15. The receptacle of claim 12 wherein the pad is a scented pad.

16. The receptacle of claim 12 wherein the receptacle is in contact with a heated surface on the air treatment device.

17. The receptacle of claim 12 wherein the pad comprises:
an upper straight perimeter;
a first side perimeter;
a second side perimeter substantially parallel to the first side perimeter;
a first lower beveled perimeter;
a second lower beveled perimeter; and
a lower straight perimeter substantially parallel to the upper straight perimeter and substantially perpendicular to the first side perimeter;
wherein the lower straight perimeter is situated between the first lower beveled perimeter and the second lower beveled perimeter.

18. The receptacle of claim 12 wherein the air treatment device is a humidifier.

19. The receptacle of claim 12 wherein the air treatment device is a heater.

20. A scented pad for insertion into a receptacle of an air treatment device, the scented pad comprising:
an upper straight perimeter;
a first side perimeter;
a second side perimeter substantially parallel to the first side perimeter;
a first lower perimeter substantially parallel to the first side perimeter;
a second lower perimeter; substantially parallel to the second side perimeter a first extension connecting the first side perimeter and the first lower perimeter;
a second extension connecting the second side perimeter and the second lower perimeter; and
a lower straight perimeter substantially parallel to the upper straight perimeter, the first extension and second extension and substantially perpendicular to the first side perimeter;
wherein the lower straight perimeter is situated between the first lower perimeter and the second lower perimeter.

* * * * *